United States Patent [19]

Don Michael

[11] Patent Number: 5,860,933
[45] Date of Patent: Jan. 19, 1999

[54] APPARATUS FOR AIDING IN THE DIAGNOSIS OF HEART CONDITIONS

[76] Inventor: T. Anthony Don Michael, 4109 Sill Pl., Bakersfield, Calif. 93306

[21] Appl. No.: 833,123

[22] Filed: Apr. 4, 1997

[51] Int. Cl.$^6$ ....................................................... A61B 5/00
[52] U.S. Cl. ............................................ 600/528; 434/266
[58] Field of Search ..................................... 600/514, 528; 434/266

[56] References Cited

U.S. PATENT DOCUMENTS

| | | | |
|---|---|---|---|
| 3,280,817 | 10/1966 | Jorgensen et al. | 600/528 |
| 3,384,981 | 5/1968 | Baessler et al. | 434/266 |
| 4,898,179 | 2/1990 | Sirota | 600/528 |

Primary Examiner—William E. Kamm
Attorney, Agent, or Firm—Pillsbury Madison & Sutro

[57] ABSTRACT

Apparatus for identifying the condition of a heart based on auscultation, comprising: a computer including a CPU, an input device, a display device and a data storage medium, wherein the data storage medium has a first storage region storing data which can be applied to the display device to provide a readable representation of one of a plurality of different heart sounds, a second storage region storing data representing heart conditions respectively associated with the different heart sounds; a third storage region storing software linking the input device and the data in the first and second storage regions for displaying on the display device a readable representation of a heart sound selected by operation of the input device and for displaying a representation of the heart condition associated with the selected heart sound.

9 Claims, 4 Drawing Sheets

APPARATUS FOR AIDING IN THE DIAGNOSIS OF HEART CONDITIONS

BACKGROUND OF THE INVENTION

The present invention relates to media, systems and a method for aiding medical professionals in the diagnosis of heart conditions.

The present invention relates more particularly to the use of heart sounds to provide such diagnoses.

The invention further relates to a system and apparatus which help to familiarize practitioners with the relation between specific heart sounds and corresponding heart conditions.

One of the oldest basic techniques employed in the practice of medicine is auscultation, which involves listening, either directly or through a stethoscope or other instrument, to heart sounds and making at least a preliminary diagnosis based thereon.

This form of diagnosis is widely used because it requires nothing more than a stethoscope which, by its nature, is highly portable and relatively inexpensive, reasonably acute hearing and the knowledge to interpret the sounds heard. Conventionally, this knowledge has been conveyed by allowing students to listen to a variety of heart sounds and instructing the students on the condition represented by each different sound. The value of this training depends to a considerable degree on the student's audible memory and very few resources are available for refreshing a practitioner's skills in this area. However, acquisition and retention of those skills is a problem, particularly when one considers that the explosion of medical knowledge has of necessity reduced the time which can be devoted to teaching auscultation in medical schools.

In light of an acknowledged need for resources which can be used to learn or relearn auscultation, various types of media providing recorded versions of various heart sounds have been placed on the market. These media include a variety of word descriptions of the individual sounds by analogy to generally known sounds. For example, such descriptions may use words such as "rough", "smooth", "train wheel", etc. to describe various heart sounds and murmurs. Of course, the manner in which these descriptions would be interpreted varies considerably from one individual to another. These known media do not permit the knowledge required to arrive at diagnoses by auscultation to be learned, or relearned, in either an acceptably short time or with the requisite degree of accuracy. Therefore, the methods and systems proposed to date fall far short of that which is needed to place the practitioner in a position to make effective use of this potentially powerful diagnostic technique.

SUMMARY OF THE INVENTION

Accordingly, it is an object of the present invention to facilitate the learning or relearning of auscultation.

A more specific object of the invention is to make full use of available phonetic systems to assist in the transition from detection of a heart sound to identification of the condition which it represents.

The above and other objects are achieved, according to the invention, by methods, apparatus, including computerized apparatus, and reference devices which provide a phonetic representation of each heart sound which is currently recognized to correspond to an identifiable condition, and a description of the condition itself. In further accordance with the invention, apparatus is provided to inform the practitioner of the position in which the patient should be placed during auscultation, the further examinations that should be made for the condition detected and treatments which may be required.

Teaching aids according to the invention may be embodied in cards having areas which bear phonetic representations of heart sounds associated with different medical conditions and areas which bear identifications of associated heart conditions, or diagnoses. The areas are associated with one another such that each phonetic representation is juxtaposed with the identification of the associated heart condition.

The phonetic representations preferably employ international phonetic notations which can be interpreted by anyone familiar with the alphabet and phonetic symbols, but not necessarily familiar with the English language.

DESCRIPTION OF THE PREFERRED EMBODIMENTS

In a computerized embodiment of the present invention, all the necessary software and data is stored on a suitable storage medium, which may be a diskette, a hard drive, a CD-ROM, a laser disk, or any other available medium having sufficient capacity.

Figure 1:
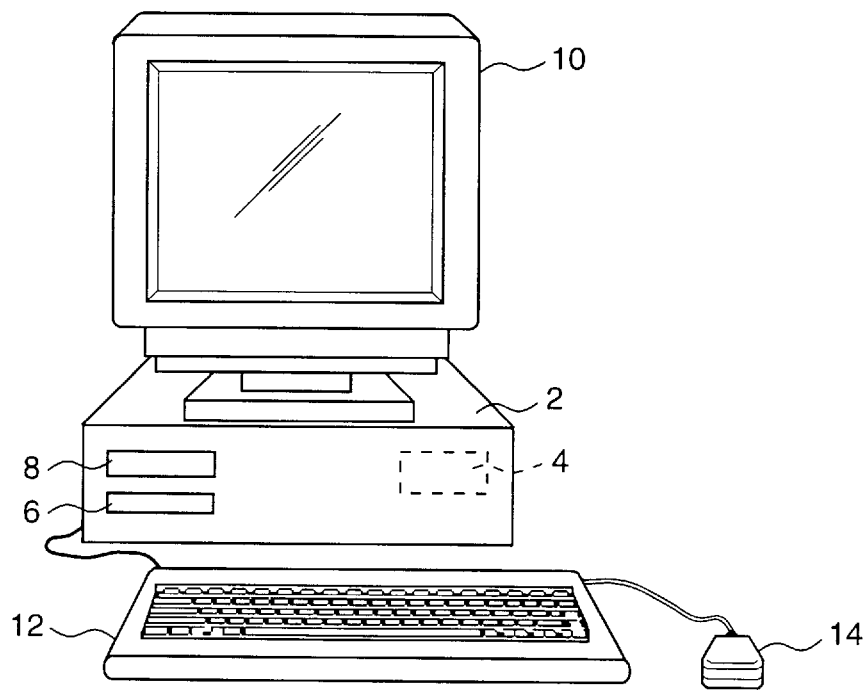
FIG. 1 is a block diagram of apparatus for implementing the present invention.

FIG. 1 is a block diagram of a conventional computer system which may constitute such a computerized embodiment. This system includes a main unit 2 containing a CPU 4, floppy disk drive 6, and CD-ROM drive 8, as well as an appropriate amount of memory and I/O devices. Minimum peripheral components include a monitor 10, a keyboard 12 and a pointing device such as a mouse 14.

The basic functions to be performed by any system according to the invention include: display of a phonetic representation of the heart sounds which are utilized for diagnosis, associated with a display of the medical condition associated with each heart sound.

It is recognized that there are 13 distinct heart sounds, one of which is the sound made by a normal heart, and the others of which are indicative of various abnormal conditions.

Recordings have been made of the sounds produced by the hearts of a large number of patients and a careful analysis of those recordings has revealed that each of the 13 heart sounds can be accurately represented by international or American English phonetic symbols, allowing any practitioner who is familiar with the phonetic system to identify any heart sound produced by a patient.

Figure 2:
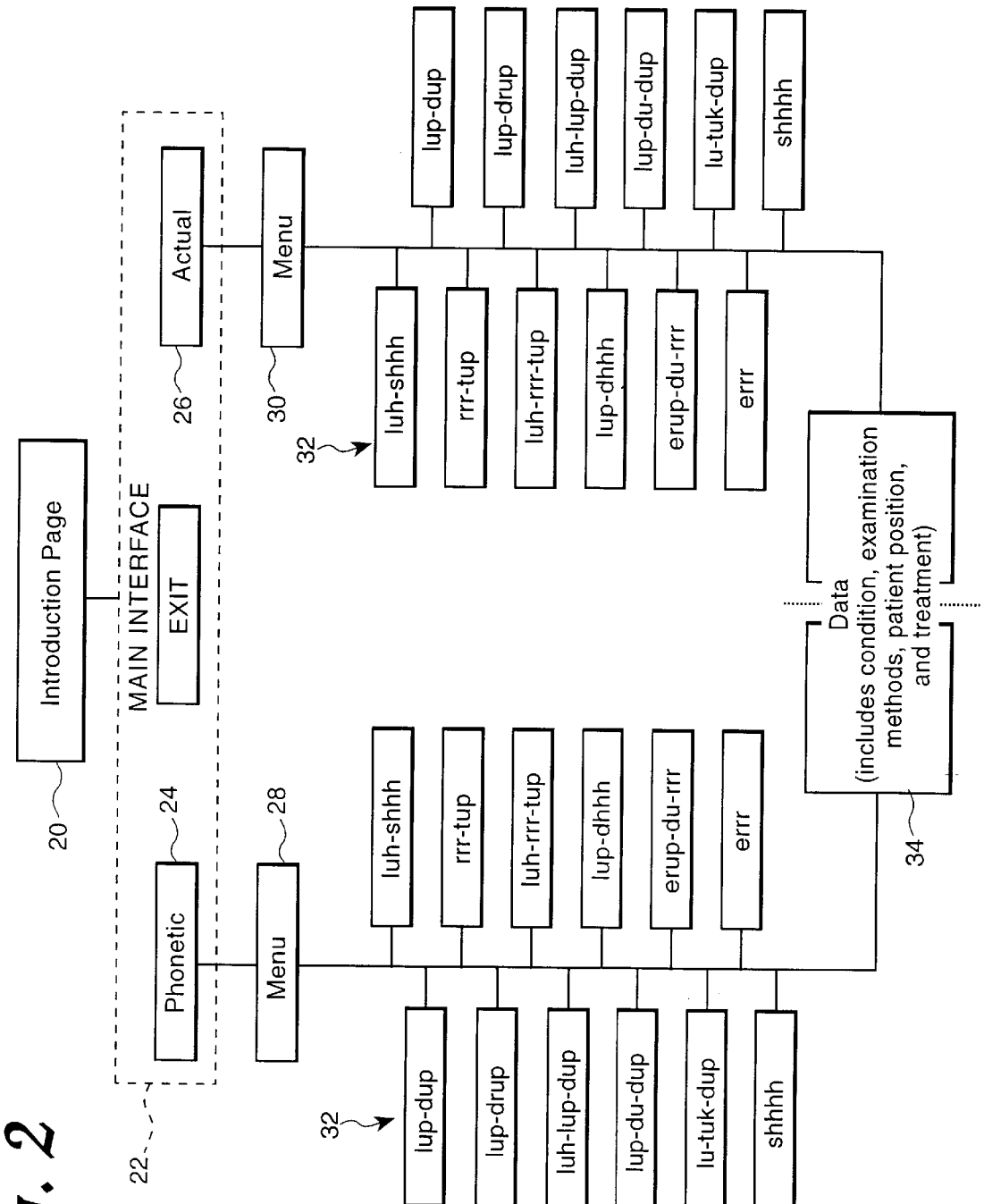
FIG. 2 is a flow diagram of a program according to the present invention.

FIG. 2 is a flow diagram illustrating the basic structure of a program implementing the present invention. The program was implemented by configuring a commercially available program sold under the name Macromedia Director, which employs the programming language known as Lingo. As shown in FIG. 2, the programming begins with the generation and display of an introduction page 20, followed by the generation and presentation of a main interface 22 having the appearance shown in FIG. 3, to be described below. This main interface offers selection of either phonetic representations 24 of the various heart sounds, or reproductions 26 of the corresponding actual heart sounds. Selection of either the phonetic representation 24 or the actual reproduction 26 invokes a respective menu 28, 30 which lists all of the heart sounds 32 according to their phonetic representations.

In connection with a selection from either menu 28 or 30, the program leads to the retrieval and display of data, which includes one or more of the medical condition represented by the heart sound, examination methods to be used, the patient position for confirming the existence of that heart sound and the indicated treatment.

The software is configured to respond to inputs, for example from keyboard 12 or pointing device 14, to display a series of screens which proceed from representations of heart sounds in various forms to a description of the condition represented by that sound, information about the position in which the patient should be placed in order to verify that the selected sound is being produced and information about further tests and/or treatments indicated by that condition.

Exemplary screens of a computer implemented embodiment of the type described above are illustrated in FIGS. 3 and 4.

Figure 3:
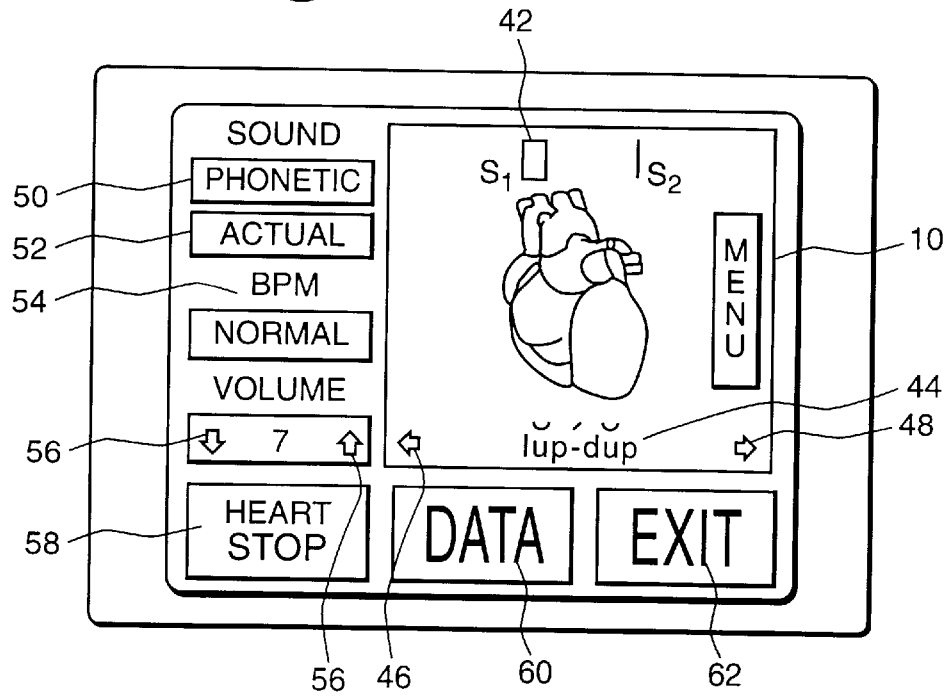
FIGS. 3 and 4 are pictorial views of two screens which appear in the operation of a method according to the invention.
Figure 4:
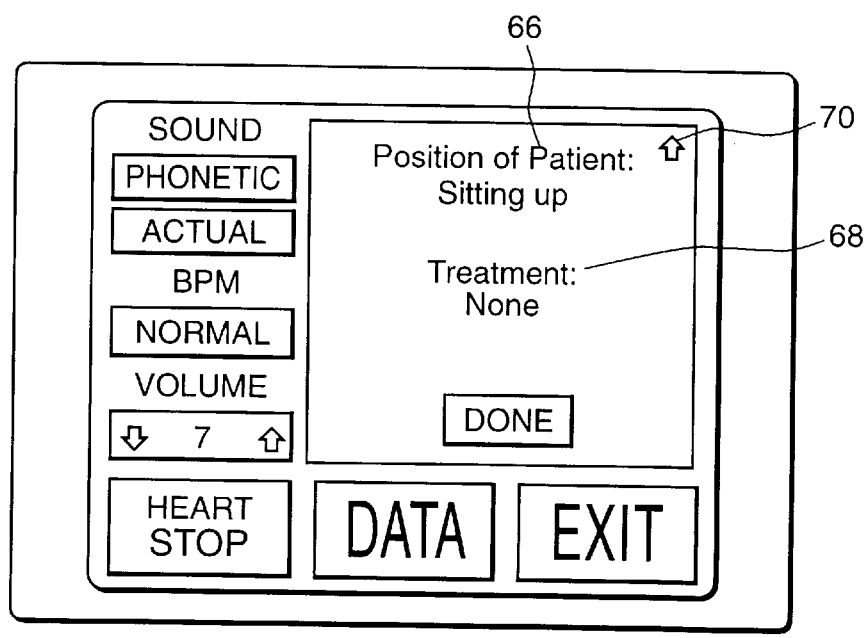

FIG. 3 shows a main interface screen and control panel including a first region 40 containing an animated display of a stylized heart, as well as a phonogram 42 and a phonetic representation 44 of a selected heart sound. That region further contains two arrows 46, 48 which, when selected by a pointing device 14, such as a mouse, inserts into this region the phonogram and phonetic representation of a subsequent heart sound.

This region is surrounded by a control area which includes, beginning from the top left, regions, or "buttons" 50, 52 for selecting either the phonetic reproduction of the presently selected heart sound or a reproduction of the heart sound itself. Below that is a button 54 which allows selection of any one of several heart rates, e.g. high, normal or low. Below that is a pair of control arrows 56 which allows selection of the volume of reproduced sounds.

At the bottom left corner of the panel is a control button 58 which can be activated via the mouse to cause the animated heart to display a simulated beating motion.

At the bottom center of the panel there is provided a data button 60 which, when activated, switches the display area of the screen to a first patient data screen (not shown) on which the condition represented by the heart sound and the further examinations to be performed are displayed. This screen further includes an arrow which, when selected with the aid of the pointing device generates a second patient data screen, shown in FIG. 4. This screen presents a description 66 of the position in which the patient should be placed to confirm that the indicated heart sound has been produced and the treatment indicated. Each of the patient display screens has an arrow 70 which enables the user to toggle between those two screens.

Returning to FIG. 3, when the user has finished consulting the information on the patient data screens about a particular heart sound, the "DONE" button in the display area is selected, resulting in a return to the main interface screen.

When the user wishes to exit the program, the "EXIT" button 62 is selected. This produces an exit screen, where the user is given an opportunity to verify the selected operation.

Any button is operated by placing a cursor on the button with the aid of the pointing device and then operating a button on the pointing device.

According to the invention, the heart sounds used for diagnosis are represented in the following phonetic forms:

| PHONETIC REPRESENTATION | INDICATED CONDITION |
| --- | --- |
| lup-dup | NORMAL $S_1 S_2$ |
| lup-drup | NORMAL SPLITTING OF $S_2$ |
| luh-lup-dup | PRESYSTOLIC GALLOP |
| lup-du-dup | PROTODIASTOLIC GALLOP |
| lu* tuk-dup | EJECTION SOUND |
| shsssh | HOLOSYSTOLIC MURMUR |
| luh-shhh | LATE SYSTOLIC MURMUR |
| rrr-tup | EARLY SYSTOLIC MURMUR |
| luh-rrr-tup | MIDSYSTOLIC MURMUR |
| lup-dhhh | EARLY DIASTOLIC MURMUR |
| erup-du du-drr | MID DIASTOLIC PRESYSTOLIC |
| e* rr* rr | CONTINUOUS MURMUR |
| tcha-tcha-tcha | PERICARDIAL RUB |

Figure 5A:
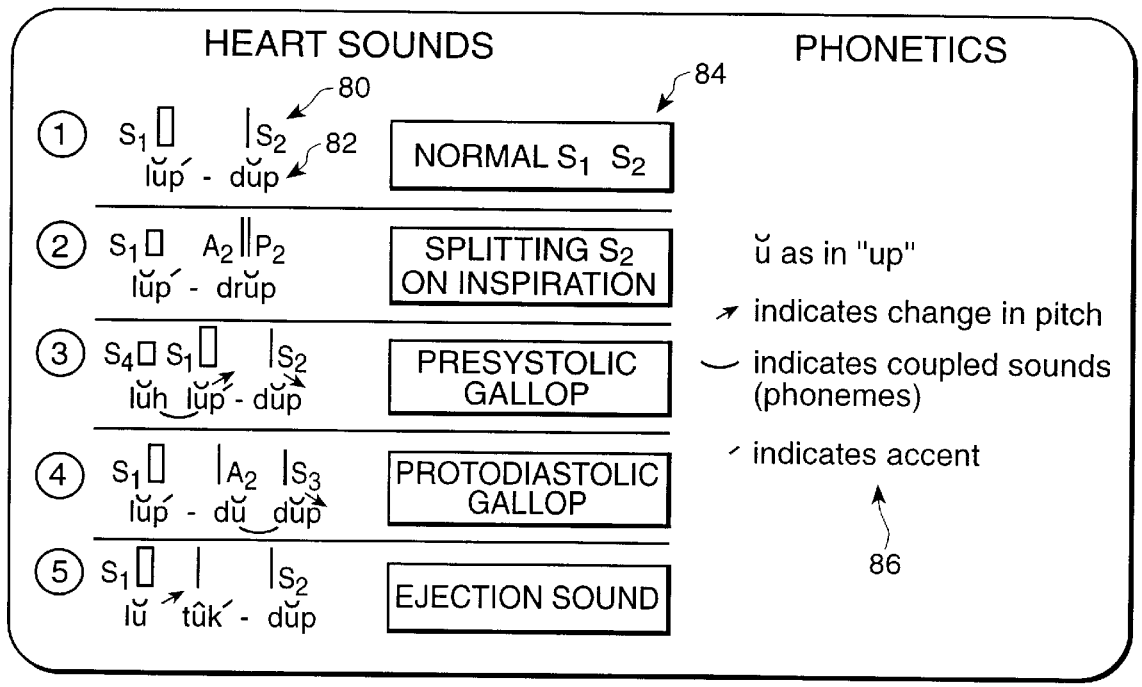
FIGS. 5A and 5B show the front and back of a display card according to the invention.
Figure 5B:
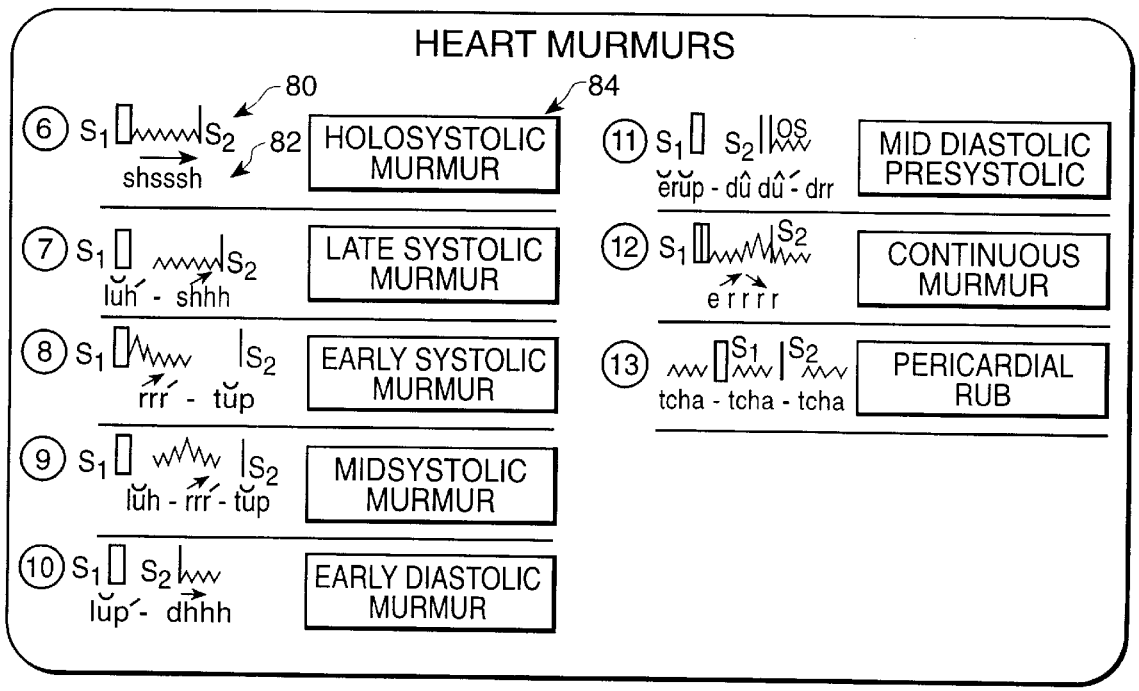

FIGS. 5A and 5B are enlarged views of the front and back, respectively, of a pocket card displaying phonograms, phonetic representations and heart condition descriptions for the heart sounds employed in medical diagnoses. The information is arranged in numbered groups 1 to 13 and within each group there is shown a phonogram 80, the associated phonetic equivalent 82, located beneath the phonogram, and the resulting condition description 84, disposed to the right of the phonogram and phonetic equivalent. Each phonetic equivalent is related to its associated phonogram in that each phonetic equivalent phoneme is disposed directly below its associated phonogram pictographic element. The phonogram symbols are conventional and the phonetic equivalents are expressed by American English phonetic symbols.

The right-hand portion of the side of the card shown in FIG. 5A also includes a key 86 to certain of the phonetic notations employed.

The side of the card shown in FIG. 5B depicts the various heart murmurs which are encountered during auscultation.

A particular feature of the card is the physical association of a phonogram, phonetic symbols and a description of the associated condition for each distinct heart sound. This enables the physician to quickly obtain a diagnosis from the sound which has been heard.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

I claim:

1. Apparatus for identifying the condition of a heart based on auscultation, comprising: a computer including a CPU, input means, display means and data storage means, wherein said data storage means comprise:

a first storage region storing data which can be applied to the display means to provide a readable representation of one of a plurality of different heart sounds;

a second storage region storing data representing heart conditions respectively associated with the different heart sounds;

a third storage region storing software linking the input means and the data in the first and second storage regions for displaying on the display means a readable representation of a heart sound selected by operation of the input means and for displaying a representation of the heart condition associated with the selected heart sound.

2. Apparatus according to claim 1 wherein said input means comprise a pointing device which controls movement of a cursor on said display means.

3. Apparatus according to claim 2 further comprising sound producing means, and wherein said storage means further comprise a fourth storage region storing data representing an audibly reproducible version of the different heart sounds, and the software stored in the third storage region is operative for producing an audible version of a selected heart sound via the sound producing means under control of the data stored in the fourth storage region in response to operation of the pointing device.

4. Apparatus according to claim 3 wherein the audibly reproducible version of the different heart sounds represented by the data stored in the fourth storage means is a spoken phonetic version of the heart sounds.

5. Apparatus according to claim 3 wherein the audibly reproducible version of the different heart sounds represented by the data stored in the fourth storage means is an audible reproduction of the heart sounds.

6. Apparatus according to claim 2 wherein said storage means further comprise a fifth storage region storing data representing medical information relating to each heart condition, and the software stored in the third storage region is operative for displaying on the display means a readable representation of the medical information relating to the heart condition associated with the selected heart sound.

7. Apparatus according to claim 6 wherein the medical information represented by the data stored in the fifth storage region identifies confirmatory tests and treatments indicated for each heart condition.

8. Apparatus according to claim 6 wherein the medical information represented by the data stored in the fifth storage region identifies the proper position for the patient during examination for each heart condition.

9. Apparatus according to claim 2 wherein the software stored in the third storage means produces a display on the display means having areas at which the cursor can be placed to control selection of a heart sound.

* * * * *